United States Patent
Tanaka

(10) Patent No.: US 9,943,458 B2
(45) Date of Patent: Apr. 17, 2018

(54) WEARABLE ACTION ASSISTING DEVICE, INTERFACE DEVICE THEREFOR, AND PROGRAM

(75) Inventor: Hiroshi Tanaka, Tsukuba (JP)

(73) Assignee: CYBERDYNE INC., Tsukuba (JP)

(*) Notice: Subject to any disclaimer, the term of this patent is extended or adjusted under 35 U.S.C. 154(b) by 874 days.

(21) Appl. No.: 13/976,894

(22) PCT Filed: Dec. 27, 2011

(86) PCT No.: PCT/JP2011/080270
§ 371 (c)(1),
(2), (4) Date: Sep. 24, 2013

(87) PCT Pub. No.: WO2012/091038
PCT Pub. Date: Jul. 5, 2012

(65) Prior Publication Data
US 2014/0012164 A1    Jan. 9, 2014

(30) Foreign Application Priority Data
Dec. 27, 2010    (JP) .................................. 2010-290769

(51) Int. Cl.
*A61H 1/02*    (2006.01)
*A61H 3/00*    (2006.01)
(Continued)

(52) U.S. Cl.
CPC .................. *A61H 3/00* (2013.01); *A61F 2/64* (2013.01); *A61F 2/72* (2013.01); *A61F 5/0125* (2013.01);
(Continued)

(58) Field of Classification Search
CPC ......... B25J 9/0006; G05B 2219/40305; A61H 1/00; A61H 2001/0211; A61H 1/0237;
(Continued)

(56) References Cited

U.S. PATENT DOCUMENTS

2003/0093021 A1* 5/2003 Goffer .................. A61F 5/0102
602/23
2003/0120183 A1* 6/2003 Simmons .................. A61F 4/00
600/595

(Continued)

FOREIGN PATENT DOCUMENTS

| CN | 1929805 A | 3/2007 |
|---|---|---|
| JP | 2005-230099 | 9/2005 |

(Continued)

OTHER PUBLICATIONS

Chinese Office Action dated Dec. 16, 2014 with English Translation; Chinese Patent Application No. 201180060331.9.

(Continued)

*Primary Examiner* — Michael Tsai
(74) *Attorney, Agent, or Firm* — Perkins Coie LLP

(57) ABSTRACT

A wearable action assisting device includes an optional control unit for generating a first instruction signal for generating power depending on a biological potential signal in a drive source, an autonomic control unit for generating a second instruction signal for generating power depending on a phase of a task of the wearer in the drive source, a generation unit for generating a drive current of the drive source based on the first and second instruction signals, a display unit having a screen displaying thereon a coordinate axis corresponding to a strength of the power, a detection unit for detecting the coordinate of a designated position in the screen, and a setting unit for extracting parameters corresponding to the detected coordinate from a table defining a correspondence between a coordinate in the screen and parameters of the signal processing, and for setting the extracted parameters in the optional control unit.

9 Claims, 11 Drawing Sheets

(51) Int. Cl.
   *B25J 9/00* (2006.01)
   *A61F 2/64* (2006.01)
   *A61F 2/72* (2006.01)
   *A61F 5/01* (2006.01)

(52) U.S. Cl.
   CPC .............. *B25J 9/0006* (2013.01); *A61H 1/024* (2013.01); *A61H 1/0244* (2013.01); *A61H 2201/5002* (2013.01); *A61H 2201/5007* (2013.01); *A61H 2201/5038* (2013.01); *A61H 2201/5046* (2013.01); *A61H 2201/5061* (2013.01); *A61H 2201/5069* (2013.01); *A61H 2230/605* (2013.01)

(58) Field of Classification Search
   CPC .... A61H 1/024; A61H 1/0244; A61H 1/0262; A61H 1/0266; A61H 2001/027; A61H 3/00; A61H 2003/001; A61H 2003/002; A61H 2003/007; A61H 3/008
   See application file for complete search history.

(56) References Cited

U.S. PATENT DOCUMENTS

| | | | |
|---|---|---|---|
| 2004/0102723 | A1 | 5/2004 | Horst |
| 2004/0249319 | A1* | 12/2004 | Dariush .................. A61H 1/00 601/5 |
| 2007/0054777 | A1* | 3/2007 | Kawai ..................... A61H 3/00 482/1 |
| 2008/0216592 | A1* | 9/2008 | Ueda ...................... B25J 9/0006 73/865.4 |
| 2008/0234608 | A1* | 9/2008 | Sankai ............... A61B 5/04888 601/5 |
| 2009/0227925 | A1* | 9/2009 | McBean ............... A61F 5/0127 602/16 |
| 2010/0121232 | A1 | 5/2010 | Sankai |
| 2010/0271051 | A1* | 10/2010 | Sankai ................. A61B 5/1038 324/679 |

FOREIGN PATENT DOCUMENTS

| | | |
|---|---|---|
| JP | 2010-017390 | 1/2010 |
| JP | 2010-263934 | 11/2010 |
| WO | WO 01/84279 | 11/2001 |
| WO | WO2002/049534 | 6/2002 |
| WO | WO2008/022435 | 2/2008 |
| WO | WO2008/123040 | 10/2008 |

OTHER PUBLICATIONS

Takao Nakai et al. "Development of Power Assistive Leg for Walking Aid using EMG and Linux", Second Asian Symposium on Industrial Automation and Robotics, BITECH, Bangkok, Thailand, May 17-18, 2001.

Extended European Search Report dated May 23, 2017 for European Patent Application No. EP 11853611 and Annex, 34 pages.

* cited by examiner

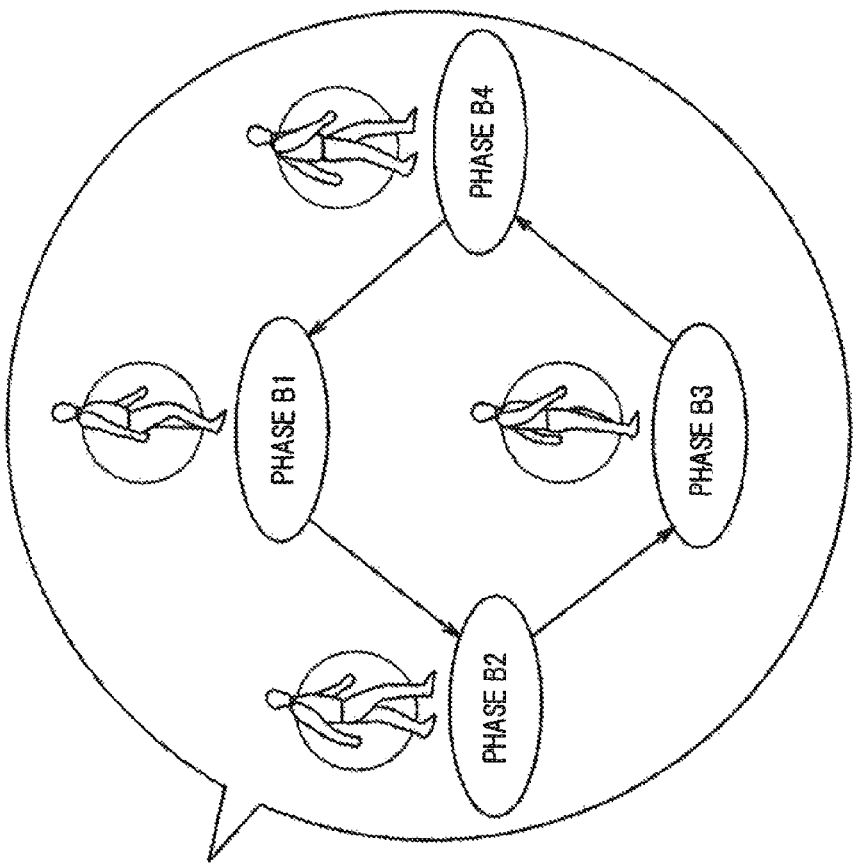
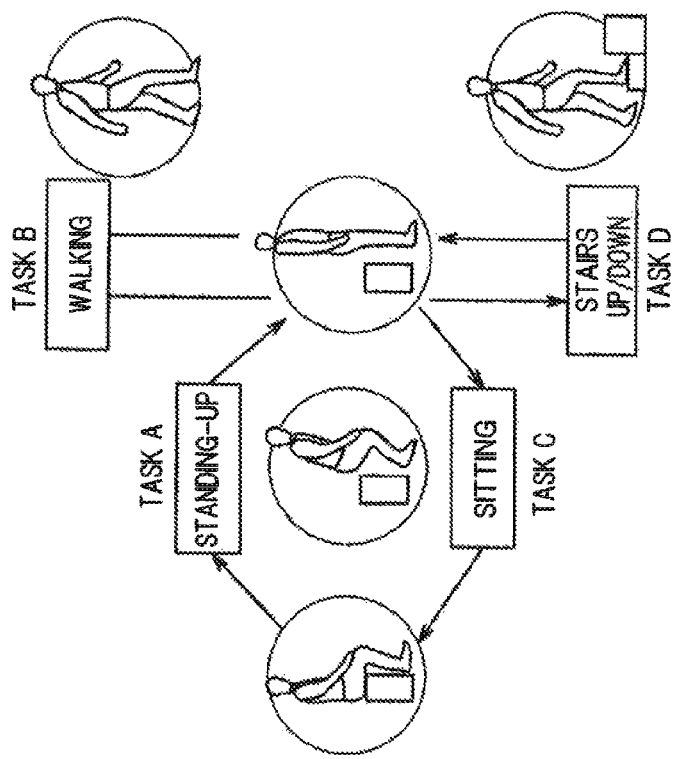
FIG. 2

| | $x_1$ | $x_2$ | $x_3$ | ... | $x_n$ |
|---|---|---|---|---|---|
| $y_1$ | $G_{11}, F_{11}$ | $G_{21}, F_{21}$ | $G_{31}, F_{31}$ | | $G_{n1}, F_{n1}$ |
| $y_2$ | $G_{12}, F_{12}$ | $G_{22}, F_{22}$ | $G_{32}, F_{32}$ | | $G_{n2}, F_{n2}$ |
| $y_3$ | $G_{13}, F_{13}$ | $G_{23}, F_{23}$ | $G_{33}, F_{33}$ | | $G_{n3}, F_{n3}$ |
| ⋮ | ⋮ | ⋮ | ⋮ | | ⋮ |
| $y_n$ | $G_{1n}, F_{1n}$ | $G_{2n}, F_{2n}$ | $G_{3n}, F_{3n}$ | ... | $G_{nn}, F_{nn}$ |

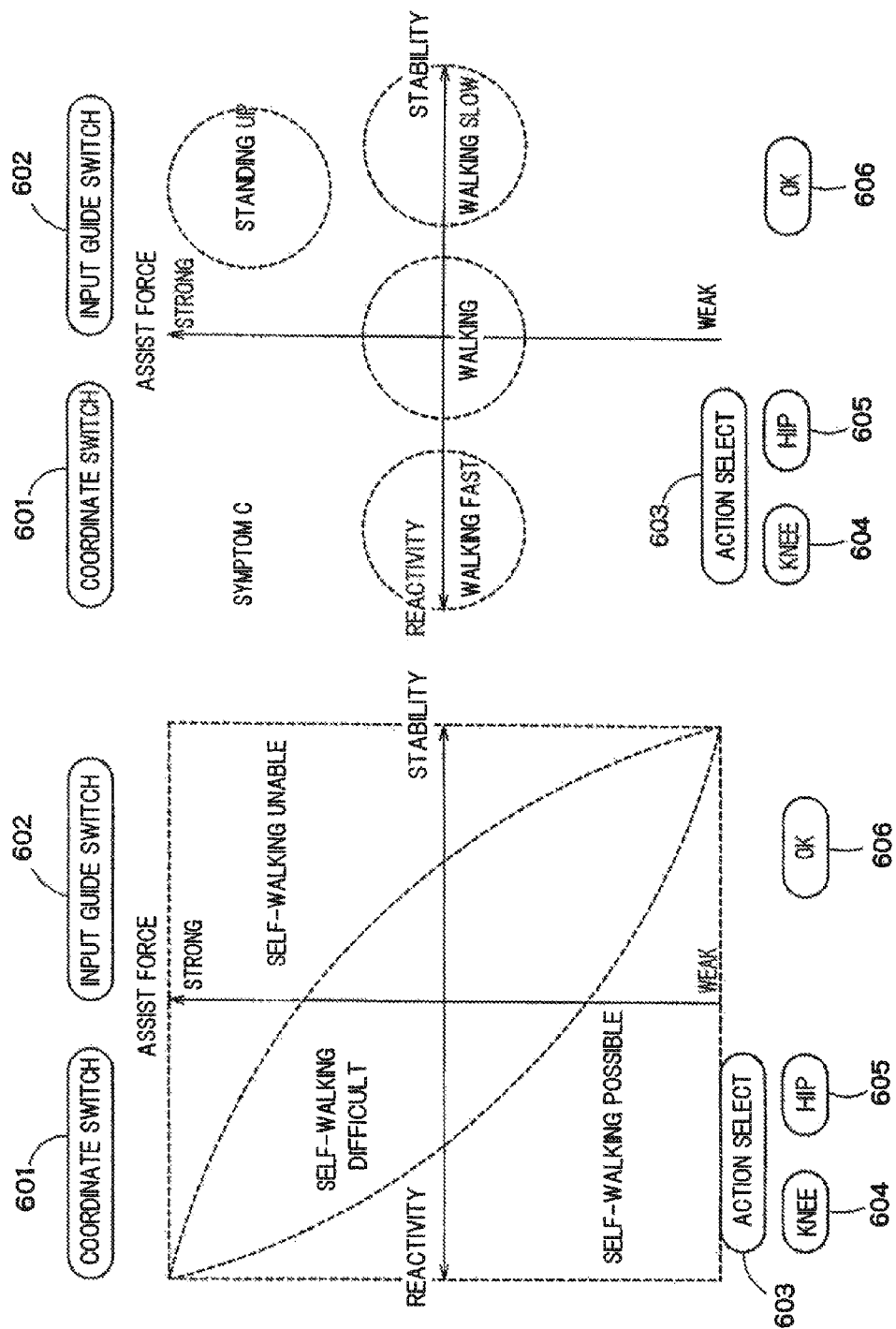

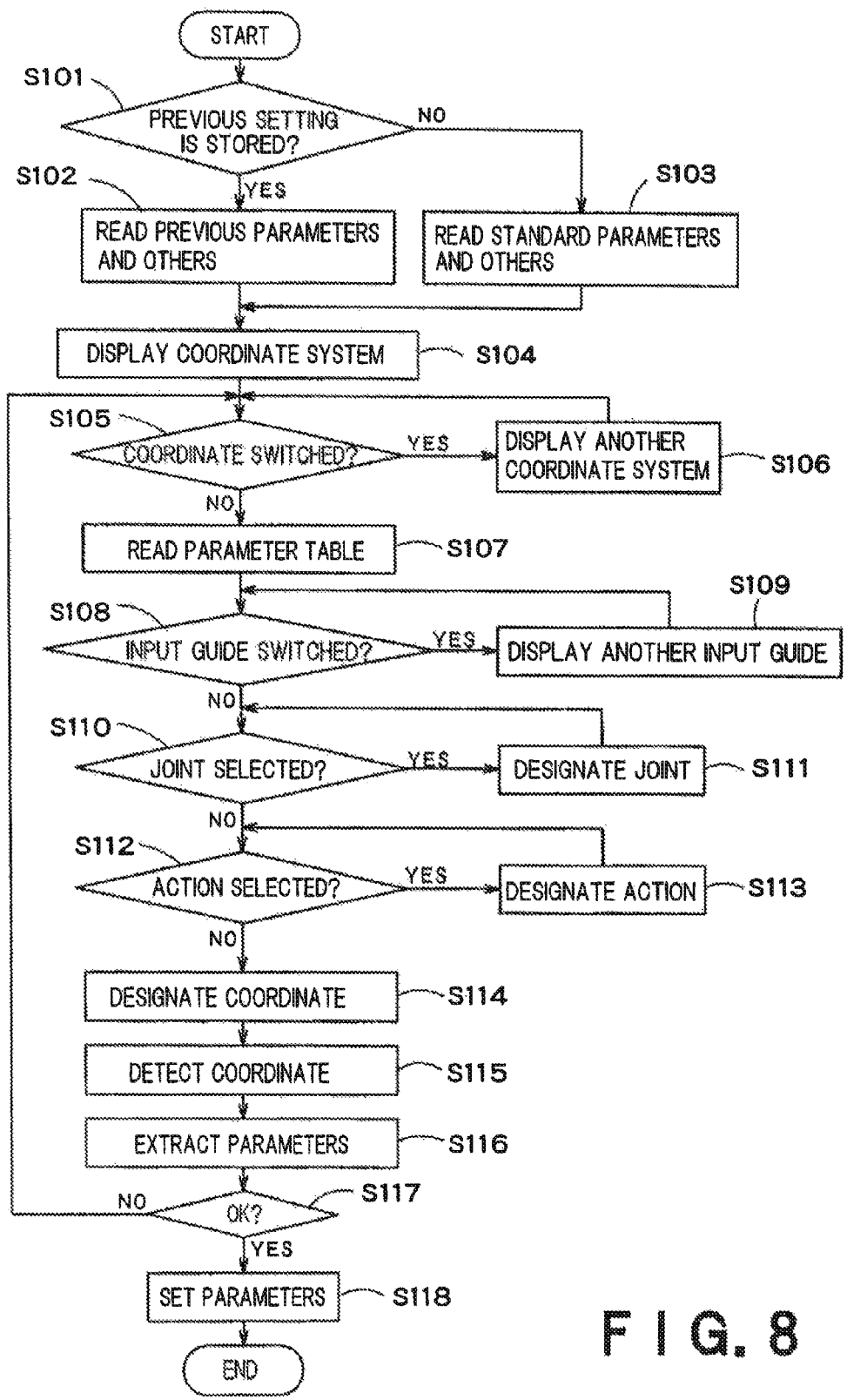
F I G. 8

| | $x_1$ | $x_2$ | $x_3$ | | $x_n$ |
|---|---|---|---|---|---|
| $y_1$ | $KF_{11}$, $KE_{11}$<br>$HF_{11}$, $HE_{11}$ | $KF_{21}$, $KE_{21}$<br>$HF_{21}$, $HE_{21}$ | $KF_{31}$, $KE_{31}$<br>$HF_{31}$, $HE_{31}$ | ... | $KF_{n1}$, $KE_{n1}$<br>$HF_{n1}$, $HE_{n1}$ |
| $y_2$ | $KF_{12}$, $KE_{12}$<br>$HF_{12}$, $HE_{12}$ | $KF_{22}$, $KE_{22}$<br>$HF_{22}$, $HE_{22}$ | $KF_{32}$, $KE_{32}$<br>$HF_{32}$, $HE_{32}$ | ... | $KF_{n2}$, $KE_{n2}$<br>$HF_{n2}$, $HE_{n2}$ |
| $y_3$ | $KF_{13}$, $KE_{13}$<br>$HF_{13}$, $HE_{13}$ | $KF_{23}$, $KE_{23}$<br>$HF_{23}$, $HE_{23}$ | $KF_{33}$, $KE_{33}$<br>$HF_{33}$, $HE_{33}$ | ... | $KF_{n3}$, $KE_{n3}$<br>$HF_{n3}$, $HE_{n3}$ |
| ... | ... | ... | ... | ... | ... |
| $y_n$ | $KF_{1n}$, $KE_{1n}$<br>$HF_{1n}$, $HE_{1n}$ | $KF_{2n}$, $KE_{2n}$<br>$HF_{2n}$, $HE_{2n}$ | $KF_{3n}$, $KE_{3n}$<br>$HF_{3n}$, $HE_{3n}$ | ... | $KF_{nn}$, $KE_{nn}$<br>$HF_{nn}$, $HE_{nn}$ |

| | $x_1 \sim x_2$ | $x_3 \sim x_4$ | ... | $x_5 \sim x_6$ | $x_7 \sim x_8$ |
|---|---|---|---|---|---|
| $y_1 \sim y_2$ | $f_{11}(x,y)$ | $f_{31}(x,y)$ | ... | $f_{51}(x,y)$ | $f_{71}(x,y)$ |
| $y_3 \sim y_4$ | $f_{13}(x,y)$ | $f_{33}(x,y)$ | ... | $f_{53}(x,y)$ | $f_{73}(x,y)$ |
| ... | ... | ... | ... | ... | ... |
| $y_5 \sim y_6$ | $f_{15}(x,y)$ | $f_{35}(x,y)$ | ... | $f_{55}(x,y)$ | $f_{75}(x,y)$ |
| $y_7 \sim y_8$ | $f_{17}(x,y)$ | $f_{37}(x,y)$ | ... | $f_{57}(x,y)$ | $f_{77}(x,y)$ |

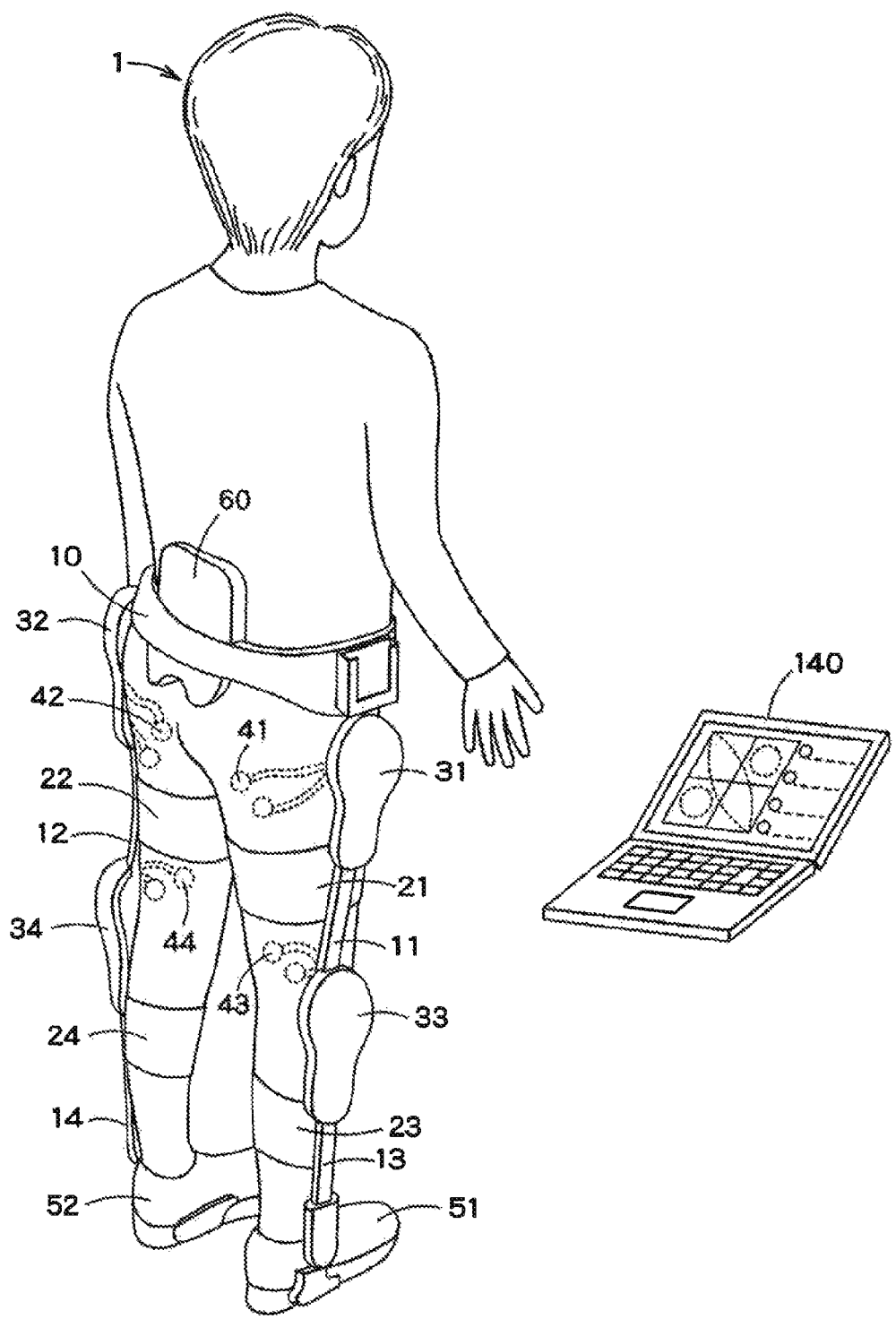
F I G. 12

WEARABLE ACTION ASSISTING DEVICE, INTERFACE DEVICE THEREFOR, AND PROGRAM

This application is a 371 of PCT/JP2011/080270 filed Dec. 27, 2011, which claims priority to Japanese Patent Application No. 2010-290769 filed Dec. 27, 2010. The entire contents of the above-identified applications are hereby incorporated by reference.

TECHNICAL FIELD

The present invention relates to a wearable action assisting device, and particularly to a wearable action assisting device for assisting or taking wearer's actions, an interface device therefor, and a program.

BACKGROUND ART

Handicapped persons or aged persons perform actions, which can be easily performed by healthy persons, with great difficulty in many cases. Thus, in these days, there is being developed various power assisting devices for assisting or taking their actions.

A wearable action assisting device (which will be simply denoted as "action assisting device" below) worn on a user (which will be denoted as "wearer" below) is known as the power assisting device, for example (see Patent Literature 1 and Non-Patent Literature 1, for example). The action assisting device comprises a myoelectric potential sensor (biological signal detection means) for detecting a myoelectric potential signal along with a wearer's muscle activity, a joint angle detection means for detecting an angular displacement of each joint of the wearer, a drive source such as drive motor for giving torque as an assist force to the wearer, and a control means for controlling the drive source.

With the action assisting device, the control means appropriately controls the drive motor based on a detection result by the myoelectric potential sensor and a detection result by the joint angle detection means so that torque according to an intention of the wearer and suitable for a current action can be given to the wearer.

When the action assisting device is worn on the wearer, various parameters are set for the action assisting device in order to give a desired assist force to the wearer. Specialized knowledge such as how the amount of change in parameter is reflected on the assist force is required for setting the parameters. Thus, there was a problem that the parameters are difficult to set.

CITATION LIST

Patent Literature

Patent Literature 1: Japanese Patent Application Laid-Open No. 2005-230099 Publication

Non-Patent Literature

Non-Patent Literature 1: Takao Nakai, Suwoong Lee, Hiroaki Kawamoto and Yoshiyuki Sankai, "Development of Power Assistive Leg for Walking Aid using EMG and Linux", Second Asian Symposium on Industrial Automation and Robotics, BITECH, Bangkok, Thailand, May 17-18, 2001

SUMMARY OF INVENTION

Technical Problem

It is an object of the present invention to provide a wearable action assisting device capable of easily setting parameters, an interface device therefor, and a program.

Solution to Problem

According to one aspect of the present invention, there is provided a wearable action assisting device comprising:
a drive source configured to give power to a wearer;
a first detection unit configured to detect a biological potential signal along with a muscle activity of the wearer;
a second detection unit configured to detect an angle of a joint of the wearer;
a first control unit configured to perform a signal processing including a filter processing and amplification on the biological potential signal, and to generate a first instruction signal for generating power depending on the biological potential signal after the signal processing on the drive source;
a first storage unit configured to store reference parameters of joint angles of the wearer corresponding to a phase configuring a task classifying an action pattern of the wearer therein;
a second control unit configured to compare a joint angle detected by the second detection unit with the reference parameters thereby to specify a phase of the action pattern of the wearer, and to generate a second instruction signal for generating power depending on the phase on the drive source;
a combination unit configured to combine the first instruction signal and the second instruction signal thereby to generate a combined instruction signal;
a generation unit configured to generate a drive current based on the combined instruction signal and supply it to the drive source;
a display unit having a screen displaying thereon a first coordinate axis corresponding to a strength of power given to the wearer by the drive source or a response speed of a change in power given to the wearer relative to a change in the biological potential signal;
an input unit configured to input an arbitrary designated position in the screen;
a third detection unit configured to detect the coordinate of the designated position;
a second storage unit configured to store parameter tables defining a correspondence between a coordinate in the screen and parameters of the signal processing in the first control unit; and
a setting unit configured to extract parameters corresponding to the detected coordinate from the parameter table and set the extracted parameters in the first control unit.

According to one aspect of the present invention, there is provided an interface device in a wearable action assisting device, the interface device for receiving an instruction of adjusting power to the wearable action assisting device, the wearable action assisting device comprising a drive source configured to give power to a wearer, a first detection unit configured to detect a biological potential signal along with a muscle activity of the wearer, a second detection unit configured to detect an angle of a joint of the wearer, a first control unit configured to perform a signal processing including a filter processing and amplification on the biological potential signal and to generate a first instruction signal for generating power depending on the biological potential signal after the signal processing on the drive source, a first storage unit configured to store reference parameters of joint angles of the wearer corresponding to a phase configuring a task classifying an action pattern of the wearer therein, a second control unit configured to compare a joint angle detected by the second detection unit with the reference parameters thereby to specify a phase of an action pattern of the wearer, and to generate a second instruction signal for generating power depending on the phase on the drive source, a combination unit configured to combine the first instruction signal and the second instruction signal to generate a combined instruction signal, a generation unit configured to generate a drive current based on the combined instruction signal and supply it to the drive source, a second storage unit configured to store parameter tables defining a correspondence between a coordinate and parameters of the signal processing in the first control unit, and a setting unit configured to extract parameters corresponding to a given coordinate from the parameter table, and set the extracted parameters in the first control unit, the wearable action assisting device comprising:

a display unit having a screen displaying thereon a coordinate axis corresponding to a strength of power given to the wearer by the drive source;

an input unit configured to input an arbitrary designated position in the screen;

a third detection unit configured to detect the coordinate of the designated position; and a communication unit configured to transmit the detected coordinate to the setting unit.

According to one aspect of the present invention, there is provided a program for causing a computer to function as an interface device for receiving an instruction of adjusting power to a wearable action assisting device, the wearable action assisting device comprising a drive source configured to give power to a wearer, a first detection unit configured to detect a biological potential signal along with a muscle activity of the wearer, a second detection unit configured to detect an angle of a joint of the wearer, a first control unit configured to perform a signal processing including a filter processing and amplification on the biological potential signal and to generate a first instruction signal for generating power depending on the biological potential signal after the signal processing on the drive source, a first storage unit configured to store reference parameters of joint angles of the wearer corresponding to a phase configuring a task classifying an action pattern of the wearer therein, a second control unit configured to compare a joint angle detected by the second detection unit with the reference parameters thereby to specify a phase of an action pattern of the wearer, and to generate a second instruction signal for generating power depending on the phase on the drive source, a combination unit configured to combine the first instruction signal and the second instruction signal to generate a combined instruction signal, a generation unit configured to generate a drive current based on the combined instruction signal and supply it to the drive source, a second storage unit configured to store parameter tables defining a correspondence between a coordinate and parameters of the signal processing in the first control unit, and a setting unit configured to extract parameters corresponding to a given coordinate from the parameter table, and set the extracted parameters in the first control unit, the program for causing a computer to perform the steps of:

displaying a coordinate axis corresponding to a strength of power given to the wearer by the drive source on a screen of a display unit;

inputting an arbitrary designated position in the screen;

detecting the coordinate of the designated position; and transmitting the detected coordinate to the setting unit.

Advantageous Effects of Invention

According to the present invention, parameters of the wearable action assisting device can be easily set.

BRIEF DESCRIPTION OF THE DRAWINGS

FIG. 2 is a diagram illustrating exemplary tasks and phases.

FIG. 7A is a diagram illustrating an exemplary display screen of the interface device.

FIG. 7B is a diagram illustrating an exemplary display screen of the interface device.

FIG. 8 is a flowchart for explaining a parameter setting method.

FIG. 9 is a diagram illustrating an exemplary parameter table.

FIG. 10 is a diagram illustrating an exemplary parameter table.

FIG. 12 is a perspective view of a state in which the wearable action assisting device according to the variant is worn as viewed from behind.

DESCRIPTION OF EMBODIMENTS

An embodiment of the present invention will be described below with reference to the drawings.

Figure 1:
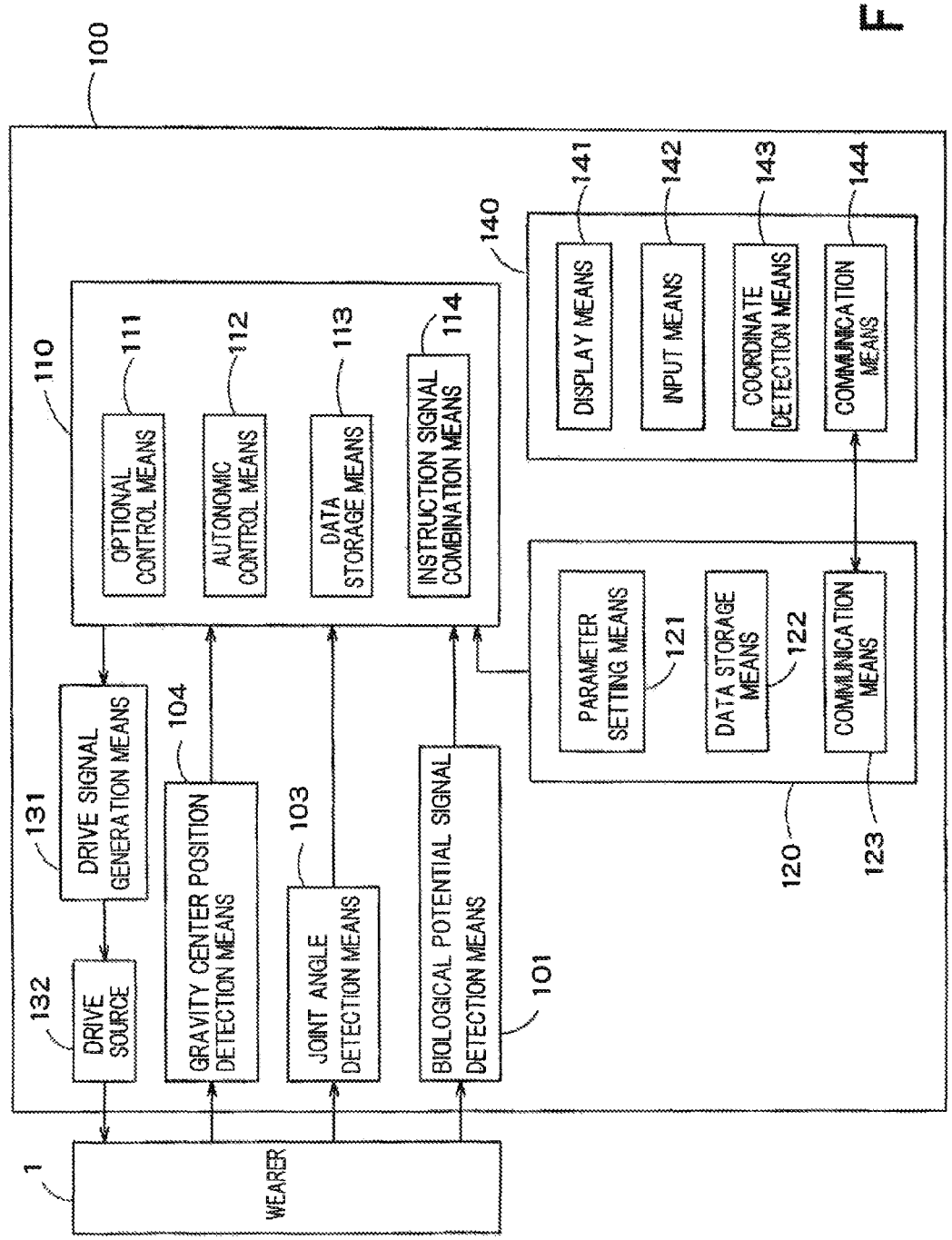
FIG. 1 is a block diagram of a wearable action assisting device according to an embodiment of the present invention.

FIG. 1 is a block diagram illustrating a control system of a wearable action assisting device according to the embodiment of the present invention. The wearable action assisting device 100 comprises a biological potential signal detection means 101, a joint angle detection means 103, a gravity center position detection means 104, a control device 110, a parameter setting device 120, a drive signal generation means 131, a drive source (actuator) 132 and an interface device 140. A wearer 1 wears the wearable action assisting device 100.

The biological potential signal detection means 101 detects a myoelectric potential in response to a muscle force generated by the wearer 1. When a person is moving, his/her intension is transmitted as an electric signal from the brain to muscles via nerves in the body. At this time, the biological potential signal detection means 101 detects a biological potential signal generated on a skin surface.

The joint angle detection means 103 detects a joint angle in response to an action of the wearer 1, and outputs it to the control device 110.

The gravity center position detection means 104 detects a gravity center position in response to an action of the wearer 1, and outputs it to the control device 110.

The control device 110 has an optional control means 111, an autonomic control means 112, a data storage means 113 and an instruction signal combination means 114.

The optional control means 111 performs a signal processing including a filter processing (smoothing processing) and amplification on a biological potential signal (myoelectric potential signal) detected by the biological potential signal detection means 101. The optional control means 111 uses the biological potential signal subjected to the signal processing to generate an optional instruction signal for generating power according to an intention of the wearer 1 on the drive source (actuator) 132. The parameters of the signal processing such as a cutoff frequency (time constant) of the filter processing and a gain of the amplification are set by the parameter setting device 120. The parameter setting method will be described later.

The data storage means 113 stores therein a reference parameter database for specifying a phase of a task of the wearer 1, and assist parameters for assisting an action of the wearer 1 according to a specified phase. The task is a classified person's main action pattern. The phase is a series of minimum action units configuring each task.

FIG. 2 illustrates exemplary tasks and phases stored in the reference parameter database.

As illustrated in FIG. 2, as the tasks for classifying the actions of the wearer 1, the reference parameter database stores therein, for example, a task A having data on a standing-up action which is a transition from a sitting state to a standing-up state, a task B having data on a walking action that the standing wearer 1 walks, a task C having data on a sitting action which is a transition from a standing-up state to a sitting state, and a task D having data on a stairs up/down action that the wearer stands up and then moves up or down stairs.

Each task is set with a plurality of items of phase data, and for example, the walking action task B is set with a phase B1 having action data when the wearer moves the right leg forward while standing with the center of gravity on the left leg (such as a trace of a joint angle or the gravity center position, a variation in torque and a change in biological potential signal), a phase B2 having action data when the moved-forward right leg lands on and the center of gravity is moved, a phase B3 having action data when the wearer stands up with the center of gravity put on the right leg, and then moves the left leg forward, and a phase B4 having action data when the wearer lands on the left leg in front of the right leg and moves the center of gravity.

In this way, when typical human actions are analyzed, it can be seen that typical action patterns such as movement of each joint's angle or gravity center in each phase are constant. Thus, typical joint angle displacements or gravity center moving states are experimentally found per phase configuring a large number of human basic actions (tasks), and are stored in the reference parameter database.

Each phase is assigned with assist patterns for multiple patterns, and each pattern is assisted in a different way even in the same phase.

For example, a person has a different walking pattern depending on a state of muscles or walking speed. Further, the walking pattern is different depending on an action purpose (such as for rehabilitation, for training, for improvement in walking, and for assist of action (force)). Thus, the most comfortable assist is different per wearer, and an assist suitable for a purpose is different. Thus, a large number of assist patterns are assigned to each phase such that an optimum assist pattern can be selected from among the assist patterns depending on a purpose assist.

The autonomic control means 112 compares parameters indicating a wearer's action state such as a joint angle detected by the joint angle detection means 103 and a gravity center position detected by the gravity center position detection means 104 with the reference parameters stored in the data storage means 113, thereby specifying a task and a phase of the action of the wearer 1. After specifying a phase depending on an action state of the wearer, the autonomic control means 112 selects an optimum assist pattern from among the assist patterns assigned to the phase according to a preset purpose, and generates an autonomic instruction signal for generating power according to the assist pattern on the drive source (actuator) 132.

The instruction signal combination means 114 combines an optional instruction signal generated by the optional control means 111 and an autonomic instruction signal generated by the autonomic control means 112, and outputs a combined instruction signal to the drive signal generation means 131. A combination ratio between the optional instruction signal and the autonomic instruction signal may be previously set per phase of each task, and may be stored in the data storage means 113.

The combined instruction signal has a waveform by which added power of power by optional control, which changes from the action start to the end, and power by autonomic control per phase is generated in the drive source 132.

The drive signal generation means 131 generates a drive signal (drive current) in response to the combined instruction signal and supplies it to the drive source 132, thereby driving the drive source 132. The drive source 132 gives an assist force (power) in response to the drive signal to the wearer 1.

The interface device 140 has a display means 141, an input means 142, a coordinate detection means 143 and a communication means 144. The interface device 140 receives an instruction for a strength of the assist force or a response speed from the wearer 1 or the like.

For example, the display means 141 displays a coordinate system (coordinate plan) in which the ordinate axis (y axis) corresponds to an assist force and the abscissa axis (x axis) corresponds to a response speed. The wearer 1 designates a position with a larger value on the ordinate axis in the coordinate system when wanting to increase the assist force, and designates a position with a smaller value on the ordinate axis when wanting to reduce the assist force via the input means 142.

The wearer 1 designates a position (on the left side of the figure) with a smaller value on the abscissa axis in the coordinate system when wanting to increase the response speed (wanting to sharpen a reaction of a given assist), and designates a position (on the right side of the figure) with a larger value on the abscissa axis when wanting to slow the response speed (wanting a reaction of a given assist to be stable) via the input means 142.

The display means 141 and the input means 142 are configured of a touch panel, for example.

The coordinate detection means 143 detects the coordinate of a position designated via the input means 142. The communication means 144 transmits the detected coordinate to the parameter setting device 120.

The parameter setting device 120 has a parameter setting means 121, a data storage means 122 and a communication means 123. The communication means 123 receives the coordinate transmitted from the communication means 144 in the interface device 140.

The data storage means 122 stores therein a parameter table indicating a correspondence between a coordinate in the coordinate plan displayed on the display means 141 and the setting values of the parameters (a gain of the amplification and a cutoff frequency of the filter processing) of the signal processing in the optional control means 111.

Figures 3, 4:
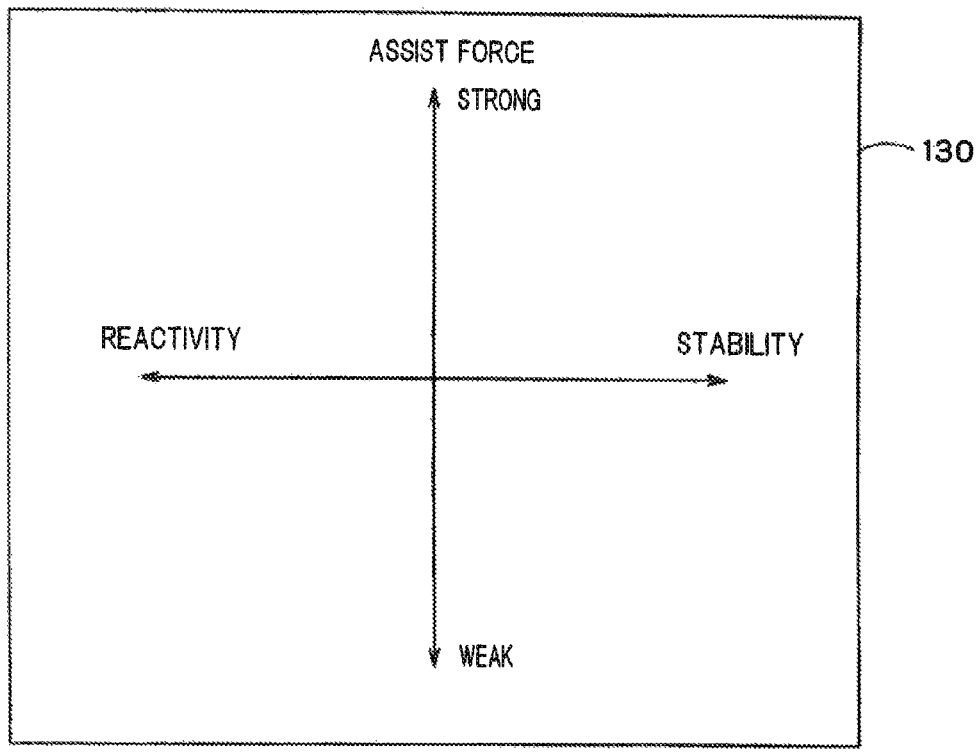
FIG. 3 is a diagram illustrating an exemplary display screen of an interface device.
FIG. 4 is a diagram illustrating an exemplary parameter table.

FIG. 4 illustrates an exemplary parameter table which is stored in the data storage means 122 and corresponds to the coordinate system illustrated in FIG. 3. $G_{ij}$ indicates a gain of the amplification set for the optional control means 111 when an input coordinate is $(x_i, y_j)$. $F_{ij}$ indicates a cutoff frequency of the filter processing set for the optional control means 111 when an input coordinate is $(x_i, y_j)$.

For example, as the value of the x coordinate is larger, the cutoff frequency $F_{ij}$ of the filter processing set for the optional control means 111 is lower. As the cutoff frequency is lower, a change in biological potential signal is gentler, and a reaction of the assist force given to the wearer 1 is more stable. As the value of the y coordinate is larger, the gain $G_{ij}$ of the amplification set for the optional control means 111 is larger. As the gain is larger, a value of the biological potential signal is larger and an assist force given to the wearer 1 is also larger.

The parameter setting means 121 extracts parameters corresponding to the coordinate received by the communication means 123 from the parameter table stored in the data storage means 122. Then, the parameter setting means 121 sets the extracted parameter in the optional control means 111.

The data storage means 122 stores therein information on a plurality of coordinate systems or touch keys displayable on the display means 141 in the interface device 140, and parameter tables according to the respective coordinate systems. The data storage means 122 stores therein information on input guides to be displayed on the coordinate. The input guides will be described later.

The communication means 123 reads the information on the coordinate system from the data storage means 122, and transmits it to the communication means 144. Thus, the interface device 140 can display various coordinate systems or touch keys.

Further, the data storage means 122 can store therein the coordinate system displayed on the display means 141 in the interface device 140 on the previous use, or a coordinate designated by the wearer 1. The communication means 123 reads the information on the previously-used coordinate from the data storage means 122 at the setting start such as power-on, and transmits it to the communication means 144. Thus, the interface device 140 can display the previously-used coordinate system on the display means 141.

Communication between the communication means 144 and the communication means 123 may be wireless communication or wired communication.

Figure 5:
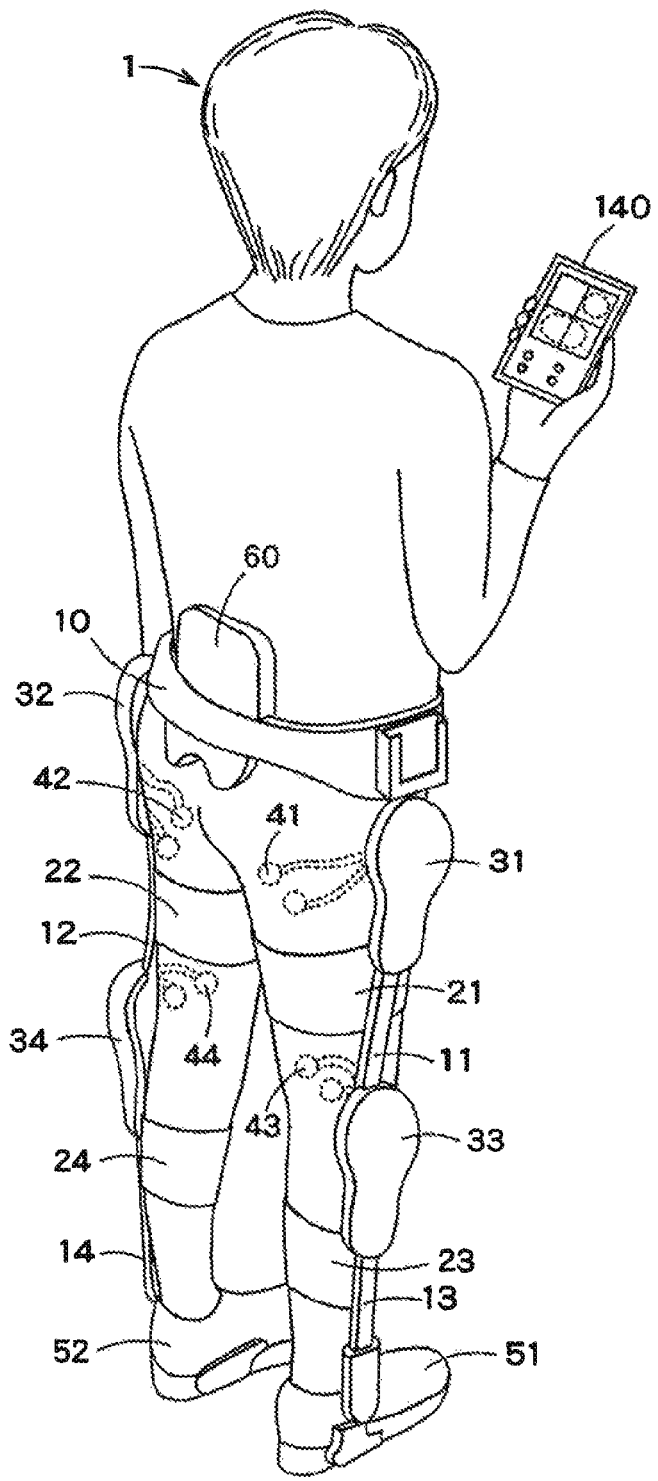
FIG. 5 is a perspective view of a state in which the wearable action assisting device according to the embodiment is worn as viewed from behind.

FIG. 5 is a perspective view of a state in which the wearable action assisting device 100 according to the present embodiment is worn as viewed from behind.

The wearable action assisting device 100 is directed for assisting a walking action of a person who is unable to walk for him/herself such as a person with lower-limb motility disorder who is unable to walk due to muscle weakness of skeletal muscle or a patient who is in rehabilitation of walking, and operates to detect a biological signal (surface myoelectric potential) occurring when a muscle force is generated in response to a signal from the brain, and to give a drive force from the actuator to the wearer 1 based on the detected biological signal.

When the wearer 1 wearing the wearable action assisting device 100 performs a walking action at his/her will, drive torque in response to a biological signal occurring at this time is given as an assist force from the action assisting device 100. Thereby, for example, he/she can walk with half of the force required for normal walking. Thus, the wearer 1 can walk while supporting his/her weight by a total force of his/her muscle force and the drive torque from the actuator.

At this time, the action assisting device 100 controls such that an intention of the wearer 1 is reflected on the assist force given in response to a movement of the center of gravity along with the walking action. Thus, the actuator in the action assisting device 100 is controlled so as to give no load against the intention of the wearer 1, and does not hinder the action of the wearer 1.

As illustrated in FIG. 5, the action assisting device 100 has a lumbar frame 10, leg frames 11 to 14, fastening belts 21 to 24, power units 31 to 34, myoelectric potential sensors 41 to 44, shoes 51, 52, and a control unit 60. The action assisting device 100 comprises a power supply (not illustrated) for supplying power to the power units 31 to 34 and the control unit 60. The power supply can be attached to the lumbar frame 10.

The lumbar frame 10 is directed for supporting the lumbar of the wearer 1, and is fixed on the trunk of the wearer 1.

The lumbar frame 10 is coupled with the power units 31 and 32 to be rotatable thereto. The power units 31 and 32 are coupled to the power units 33 and 34 via the lumbar frames 11 and 12, respectively. The power units 33 and 34 are coupled to be rotatable to the lumbar frames 11, 12, respectively.

The shoes 51 and 52 are coupled to the power units 33 and 34 via the frames 13 and 14, respectively. All the weight of the action assisting device 100 is supported by the shoes 51 and 52, and thus is not applied on the wearer 1.

The power units 31 to 34 are provided on the parts corresponding to the respective joints (hip joints and knee joints) of the thighs and the lower thighs. The frames 11 and 12 are provided along the outsides of the thighs of the wearer 1, and the frames 13 and 14 are provided along the outsides of the shanks of the wearer 1. Thus, the frames 11 to 14 are configured to perform the same actions as the legs of the wearer 1.

The frames 11 and 12 are fastened on the thighs of the wearer 1 by the fastening belts 21 and 22, respectively. The frames 13 and 14 are fastened below the knees of the wearer 1 by the fastening belts 23 and 24, respectively.

The power units 31 to 34 each include a drive motor, and a rotation shaft of the drive motor transmits drive torque to the frames 11 to 14 to be driven via a gear, respectively. The drive torque is transmitted as an assist force to the legs of the wearer 1 via the fastening belts 21 to 24.

The drive motor has an angle sensor for detecting a joint angle. The angle sensor is configured of a rotary encoder for counting pulses in proportion to a joint angle, for example. The angle sensor outputs the detected joint angle to the control unit 60.

The power units 31 to 34 correspond to the joint angle detection means 103, the drive signal generation means 131 and the drive source 132 in FIG. 1.

The myoelectric potential sensors 41 and 42 are attached on the hip of the wearer 1, and detect a surface myoelectric potential of the gluteus maximus muscles. Thereby, a myoelectric potential depending on a kick-back force or a muscle force on rise of stairs is detected, for example.

The myoelectric potential sensors 43 and 44 are attached on the back sides of the legs above the knees to detect surface potentials of the biceps femoris muscles, respectively. Thereby, a myoelectric potential in response to the muscle force for moving a below-knee part backward is detected.

Though not illustrated, there are also provided myoelectric potential sensors which are attached on the front sides of the roots of the thighs of the wearer 1 and detect the surface myoelectric potentials of the iliopsoas muscles thereby to detect myoelectric potentials depending on the muscle force for moving a leg forward, and myoelectric potential sensors which are attached on the front sides of the legs above the knees of the wearer 1 and detect surface myoelectric potentials of the quadriceps femoris muscles to thereby detect myoelectric potentials depending on the muscle force for moving a below-knee part forward.

The myoelectric potential sensors output the detected myoelectric potentials to the control unit 60. The myoelectric potential sensors 41 to 44 correspond to the biological potential signal detection means 101.

The shoes 51 and 52 are provided with sole insert sensors (not illustrated). The sole insert sensors include reaction sensors for detecting reactions on the front sides and back sides of the right leg and the left leg, for example. The reaction sensor is made of a piezoelectric device for outputting a voltage depending on an applied load, for example, thereby detecting a position of the center of gravity. The sole insert sensor outputs a detection result to the control unit 60. The sole insert sensors correspond to the gravity center position detection means 104.

The wearer 1 can adjust the assist force and the response speed to desired values by use of the interface device 140. The control unit 60 corresponds to the control device 110 and the parameter setting device 120.

Figures 6A, 6B:
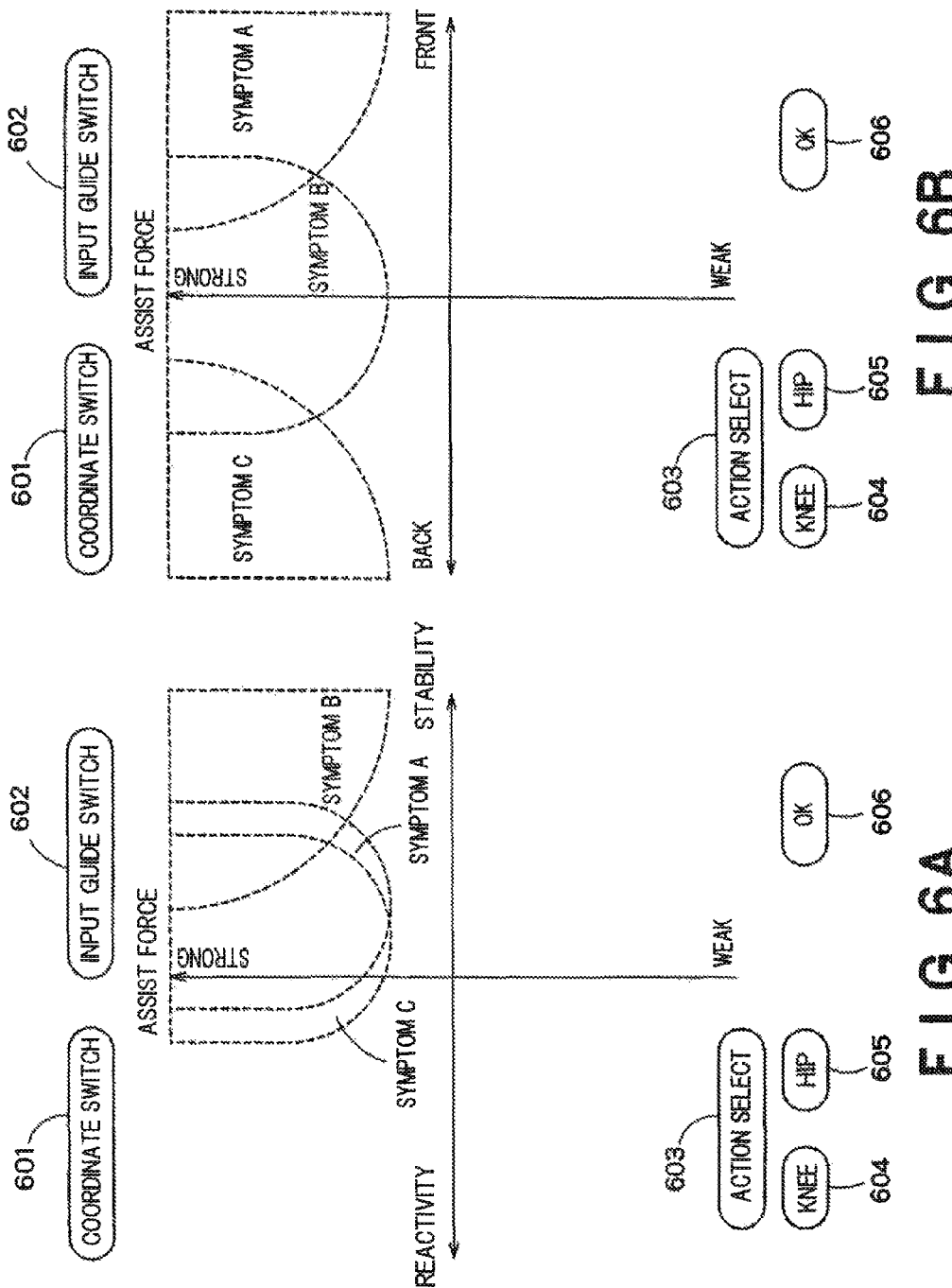
FIG. 6A is a diagram illustrating an exemplary display screen of the interface device.
FIG. 6B is a diagram illustrating an exemplary display screen of the interface device.

A method for adjusting the assist force and the like by the interface device 140 will be described below. FIG. 6A illustrates an exemplary screen displayed on a touch panel corresponding to the display means 141 and the input means 142 in the interface device 140. As illustrated in FIG. 6A, the touch panel displays thereon a coordinate system (coordinate axes) in which the ordinate axis corresponds to the assist force and the abscissa axis corresponds to the response speed.

When the wearer 1 designates any position on the screen, the coordinate of the position is detected and is transmitted to the parameter setting device 120. The parameter setting device extracts the parameters corresponding to the coordinate from the parameter table as described above.

The touch panel displays thereon a coordinate switch key 601, an input guide switch key 602, an action select key 603, a knee joint select key 604, a hip joint select key 605, and an OK key 606

The coordinate switch key 601 is pressed to switch the coordinate axes to be displayed. For example, the coordinate switch key 601 on the display screen in FIG. 6A is pressed so that the coordinate system is switched to one illustrated in FIG. 6B. In the coordinate system illustrated in FIG. 6B, the ordinate axis (y axis) corresponds to the assist force and the abscissa axis (x axis) corresponds to a front/back balance by assist. For the front/back balance, the front side (the right side of figure) is designated so that a reaction to a force for moving a joint forward is made stronger, and the back side (the left side of figure) is designated so that a reaction to a force for moving a joint backward is made stronger.

The touch panel displays thereon a region suitable for a symptom or state of the wearer 1 as an input guide. FIGS. 6A and 6B illustrate suitable regions for the symptoms A to C.

The region for symptom A is suitable for a person who is weak in muscles for moving the legs forward, and an assist in the bending direction of the hip joints and an assist in the extending direction of the knee joints are set to be strong in order to enable the legs to be easily moved forward.

The region for symptom B is suitable for a person who is weak in both the front and back muscles, and the assists for the knee joints and the hip joints of both the legs are set at the same level.

The region for symptom C is suitable for a person who is weak in a force for moving the legs backward, and an assist in the extending direction of the hip joints and an assist in the bending direction of the knee joints are set to be strong in order to enable the legs to be moved backward.

As can be seen from FIG. 6A and 6B, the positions of the suitable regions are different between FIGS. 6A and 6B with the different coordinate systems even for the same symptom. The wearer 1 designates a region indicated by the input guide depending on his/her symptom, and thus is given a proper assist force.

The knee joint select key 604 or the hip joint select key 605 is pressed so that a strength of an assist for each joint can be individually set. When a joint is not designated, the knee joint/hip joint assists are set at the same level.

The OK key 606 is pressed so that the parameter setting means 121 sets the extracted parameters in the optional control means 111 as described above.

The input guide switch key 602 is pressed to switch an input guide to be displayed. For example, FIG. 7A illustrates a region depending on a self-walking ability as an input guide. The input guide switch key 602 is pressed on the display screen in FIG. 7A so that an input guide depending on a purpose action is displayed as illustrated in FIG. 7B.

The action select key 603 is pressed to select an action to be subjected to the parameter setting. For example, on the display screen in FIG. 7B, a standing-up action or walking action can be selected as an action to be subjected to the parameter setting.

Such a parameter setting method using the interface device 140 will be described in the flowchart illustrated in FIG. 8.

(Step S101) When the power supply is turned on and the parameter setting operation is started, whether the previously-used parameters and the like are stored in the data storage means 122 in the parameter setting device 120 is detected. When stored, the processing proceeds to step 102, and when not stored, the processing proceeds to step S103.

(Step S102) The previously-used coordinate system displayed on the display means 141 in the interface device 140, the used parameter table, the parameters and the like are read from the data storage means 122.

(Step S103) A previously-stored standard coordinate system, a parameter table, the parameters and the like are read from the data storage means 122.

(Step S104) The coordinate system is displayed on the display means 141.

Specifically, the communication means 123 transmits information on the coordinate system read from the data storage means 122 in step S102 or S103, the input guide, the touch keys and the like to the communication means 144. Then, the display means 141 displays the coordinate system, the input guide, the touch keys, and the like based on the information received by the communication means 144.

(Step S105) When the coordinate switch key 601 is pressed, the processing proceeds to step S106, and when not pressed, the processing proceeds to step S107.

(Step S106) A different coordinate system is displayed on the display means 141.

Specifically, the communication means 144 notifies that a coordinate switch instruction has been made to the communication means 123. The communication means 123 reads information on the different coordinate system from the coordinate system displayed on the display means 141 from the data storage means 122, and transmits it to the communication means 144. Then, the display means 141 displays thereon the different coordinate system based on the information received from the communication means 144.

Steps S105 and S106 are repeated until a desired coordinate system is displayed on the display means 141.

(Step S107) The parameter setting means 121 reads a parameter table corresponding to the coordinate system displayed on the display means 141. For example, when the coordinate system illustrated in FIG. 6A is displayed on the display means 141, the parameter table illustrated in FIG. 4 is read.

When the coordinate system illustrated in FIG. 6B is displayed on the display means 141, the parameter table illustrated in FIG. 9 is read. $KF_{ij}$ indicates amplification (gain) of a myoelectric potential corresponding to the bending of a knee joint in the optional control means 111 when the input coordinate is $(x_i, y_j)$.

The $KE_{ij}$ indicates amplification (gain) of a myoelectric potential corresponding to the extending of a knee joint in the optional control means 111 when the input coordinate is $(x_i, y_j)$.

$HF_{ij}$ indicates amplification (gain) of a myoelectric potential corresponding to the bending of a hip joint in the optional control means 111 when the input coordinate is $(x_i, y_j)$.

$HE_{ij}$ indicates amplification (gain) of a myoelectric potential corresponding to the extending of a hip joint in the optional control means 111 when the input coordinate is $(x_i, y_j)$.

The parameter setting means 121 may further read the parameter table recording therein a plurality of assist patterns for the autonomic control means 112 as illustrated in FIG. 10. Such a parameter table is prepared for each phase. In FIG. 10, $f_{11}(x, y)$ to $f_{nm}(x, y)$ are the functions indicating the respective assist patterns, and indicate a torque output pattern, a joint angle trace pattern, and the like. When the autonomic control means 112 specifies a phase, a parameter table corresponding to the specified phase is read. Then, the assist parameters are selected from the read parameter table based on the input coordinate. The autonomic control means 112 generates an autonomic instruction signal depending on the selected assist parameters.

(Step S108) When the input guide switch key 602 is pressed, the processing proceeds to step S109, and when not pressed, the processing proceeds to step S110.

(Step S109) A different input guide is displayed on the display means 141.

Specifically, the communication means 144 notifies that an input guide switch instruction has been made to the communication means 123. The communication means 123 reads information on the different input guide from the input guide displayed on the display means 141 from the data storage means 122, and transmits it to the communication means 144. The display means 141 displays the different input guide based on the information received from the communication means 144.

(Step S110) When the knee joint select key 604/hip joint select key 605 is pressed, the processing proceeds to step S111, and when not pressed, the processing proceeds to step S112.

(Step S111) A gain of amplification of the optional control means 111 or a cutoff frequency of the filter processing for processing a myoelectric potential corresponding to the joint selected in step S110 is designated to be subjected to the parameter setting.

(Step S112) When the action select key 603 is pressed, the processing proceeds to step S113, and when not pressed, the processing proceeds to step S114.

(Step S113) An action to be subjected to the parameter setting is designated. An action to be designated is a walking action, a standing-up action, a sitting action, or the like, for example.

(Step S114) An arbitrary coordinate on the coordinate system displayed on the display means 141 is designated by the wearer 1.

(Step S115) The coordinate detection means 143 detects the coordinate designated in step S114. Then, the communication means 144 transmits the detected coordinate to the communication means 123.

(Step 116) The parameter setting means 121 receives the coordinate detected in step S115 from the communication means 123. Then, the parameter setting means 121 extracts the parameters corresponding to the coordinate with reference to the parameter table.

(Step S117) When the OK key 606 is pressed, the processing proceeds to step S118, and when not pressed, the processing returns to step S105.

(Step S118) The parameter setting means 121 sets the parameters extracted in step S116 in the optional control means 111.

The wearer designates a desired coordinate on the coordinate system displayed in the interface device 140, thereby adjusting and setting the assist force, the assist balance, the response speed and the like. When setting the parameters, the wearer can set the parameters even if he/she has no specialized knowledge such as how the amount of change in parameter is reflected on the assist force.

In this way, the interface device in the wearable action assisting device according to the present embodiment is used, thereby easily setting the parameters of the wearable action assisting device.

There has been described in the above embodiment the example that the display means 141 and the input means 142 in the interface device are a touch panel, but a liquid crystal screen or the like of the display means 141 displays thereon a cursor, and a coordinate or the like may be designated by moving the cursor by use of the button of the input means 142.

Figure 11:
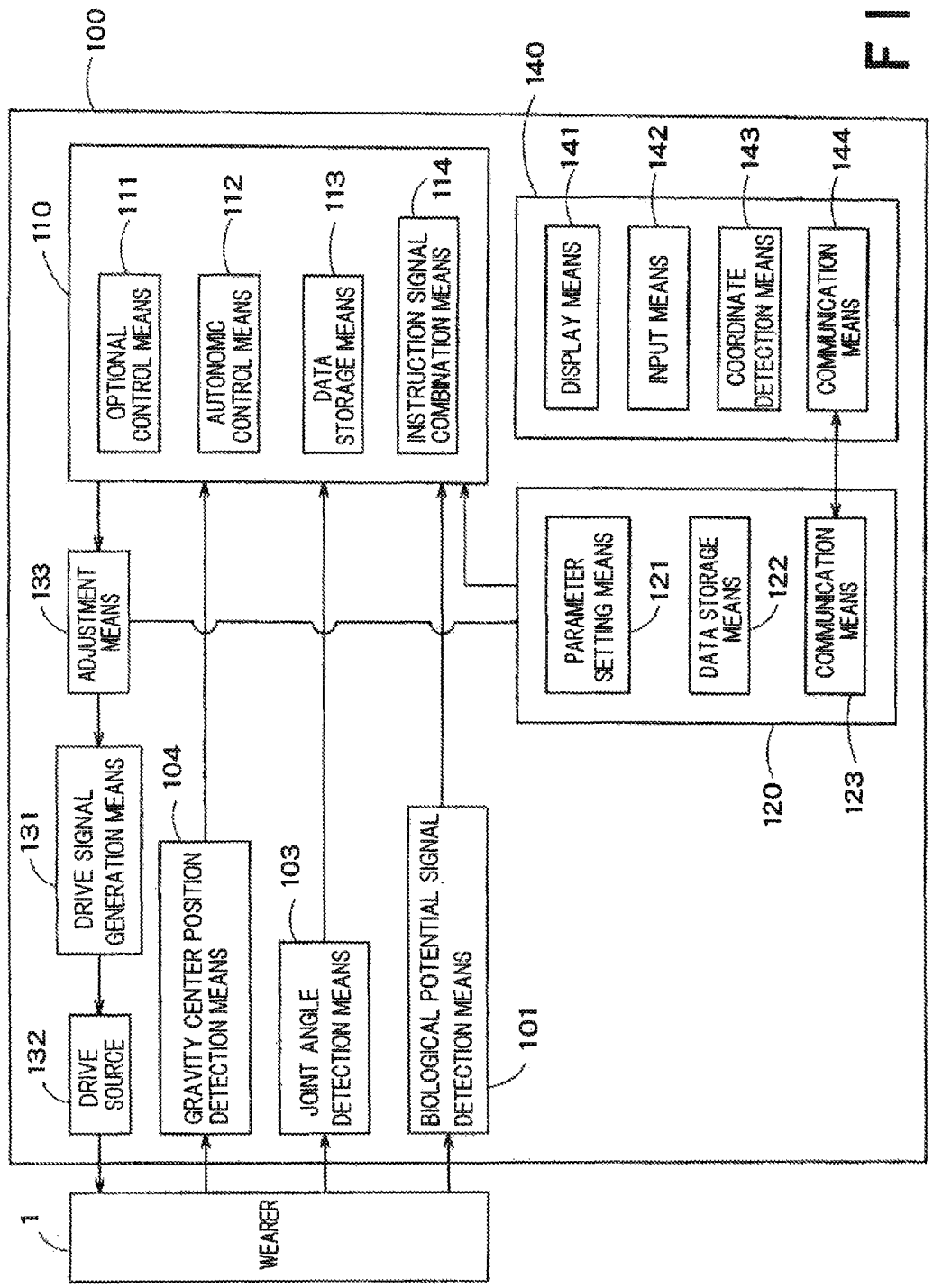
FIG. 11 is a block diagram of a wearable action assisting device according to a variant.

As illustrated in FIG. 11, an adjustment means 133 for adjusting a combined instruction signal output from the control device 110 may be provided between the control device 110 and the drive signal generation means 131 so that the parameter setting device 120 may set the parameters of an amplifier included in the adjustment means 133. Even with the structure, the strength of the assist can be adjusted.

While the parameter tables are stored in the data storage means 122 in the above embodiment, the functions for calculating the parameters may be stored therein. When receiving a coordinate from the interface device 140, the parameter setting means 121 inputs the values of x and y of the coordinate into the function thereby to calculate the parameters to be set in the optional control means 111.

While the display means 141 displays thereon the two axes of the ordinate axis and the abscissa axis in the above embodiment, only one axis may be displayed. For example, the display means 141 displays only an axis for adjusting the strength of the assist force. In this case, it is suitable that the data storage means 122 stores therein a parameter table corresponding to only the coordinate with one axis. Alternatively, the display means 141 may display only the axis for adjusting the response speed when power given to the wearer 1 changes along with a change in biological potential signal.

At least part of the interface device 140 described in the above embodiment may be configured in hardware, or may be configured in software. When it is configured in software, a program for realizing at least part of the functions of the interface device 140 may be stored in a recording medium such as flexible disk or CD-ROM, and may be read in a computer to be executed as illustrated in FIG. 12. The recording medium is not limited to removable mediums such as magnetic disk or optical disk, and may be a fixed recording medium such as hard disk device or memory.

A program for realizing at least part of the functions of the interface device 140 may be distributed via a communication line (including wireless communication) such as Internet. Further, the program may be distributed in a wired manner such as Internet, or a wireless manner, or via a recording medium while being encrypted, modulated or compressed.

The present invention is not limited to the embodiment, and the constituents may be modified and embodied in the embodiment stage without departing from the spirit of the invention. Further, a plurality of constituents disclosed in the above embodiment may be appropriately combined thereby to form various inventions. For example, some constituents may be deleted from all the constituents illustrated by the embodiment. Furthermore, constituents for different embodiments may be appropriately combined.

REFERENCE SIGNS LIST

100: Wearable action assisting device
101: Biological potential signal detection means
103: Joint angle detection means
104: Gravity center position detection means
110: Control device
120: Parameter setting device
131: Drive signal generation means
132: Drive source (actuator)
140: Interface device

What is claimed is:

1. A wearable action assisting device comprising:
a drive source configured to give power to a wearer;
a first detection unit configured to detect a biological potential signal along with a muscle activity of the wearer;
a second detection unit configured to detect an angle of a joint of the wearer;
a first control unit configured to perform a signal processing including a filter processing and amplification on the biological potential signal, and to generate a first instruction signal for generating power depending on the biological potential signal after the signal processing on the drive source;
a first storage unit configured to store reference parameters of joint angles of the wearer corresponding to a phase configuring a task classifying an action pattern of the wearer therein;
a second control unit configured to compare a joint angle detected by the second detection unit with said reference parameters thereby to specify a phase of the action pattern of the wearer, and to generate a second instruction signal for generating power depending on the phase on the drive source;
a combination unit configured to combine the first instruction signal and the second instruction signal thereby to generate a combined instruction signal;
a generation unit configured to generate a drive current based on the combined instruction signal and supply it to the drive source;
a display unit having a screen displaying thereon a first coordinate axis corresponding to a strength of power given to the wearer by the drive source or a response speed of a change in power given to the wearer relative to a change in the biological potential signal;
an input unit configured to input an arbitrary designated position in the screen;
a third detection unit configured to detect the coordinate of the designated position;
a second storage unit configured to store a parameter table defining a correspondence between a coordinate in the screen and parameters of the signal processing in the first control unit; and
a setting unit configured to extract parameters corresponding to the detected coordinate from the parameter table and set the extracted parameters in the first control unit.

2. The wearable action assisting device according to claim 1,
wherein the first coordinate axis corresponds to a strength of power given to the wearer by the drive source,
the parameter table defines a correspondence between a coordinate in the screen and a gain of amplification in the first control unit, and
the setting unit extracts a gain corresponding to the detected coordinate from the parameter table, and sets the extracted gain in the first control unit.

3. The wearable action assisting device according to claim 1,
wherein the first coordinate axis corresponds to a response speed of a change in power given to the wearer relative to a change in the biological potential signal,
the parameter table defines a correspondence between a coordinate in the screen and a cutoff frequency of a filter processing in the first control unit, and
the setting unit extracts a cutoff frequency corresponding to the detected coordinate from the parameter table, and sets the extracted cutoff frequency in the first control unit.

4. The wearable action assisting device according to claim 2,
wherein the display unit further displays a second coordinate axis corresponding to a response speed of a change in power given to the wearer relative to a change in the biological potential signal,
the parameter table defines a correspondence between a coordinate in the screen and a cutoff frequency of a filter processing in the first control unit, and
the setting unit extracts a cutoff frequency corresponding to the detected coordinate from the parameter table, and sets the extracted cutoff frequency in the first control unit.

5. The wearable action assisting device according to claim 1,
wherein the display unit further displays a second coordinate axis corresponding to a front/back balance of power given to the wearer,
the parameter table defines a correspondence between a coordinate in the screen and a gain of amplification of the biological potential signal corresponding to each of extending of a knee joint of the wearer, bending of a knee joint, extending of a hip joint and bending of a hip joint, and
the setting unit extracts a gain of each of the extending of a knee joint, the bending of a knee joint, the extending of a hip joint and the bending of a hip joint corresponding to the detected coordinate from the parameter table, and sets the extracted gain in the first control unit.

6. The wearable action assisting device according to claim 4,
wherein the display unit displays a third coordinate axis corresponding to a front/back balance of power given to the wearer,
the input unit receives an instruction of switching one or two coordinate axes displayed on the display unit among the first to third coordinate axes,
the parameter table defines a correspondence between a coordinate in the screen and a gain of amplification of the biological potential signal corresponding to each of extending of a knee joint of the wearer, bending of a knee joint, extending of a hip joint and bending of a hip joint, and
when the third coordinate axis is displayed on the display unit, the setting unit extracts a gain of each of the extending of a knee joint, the bending of a knee joint, the extending of a hip joint and the bending of a hip joint corresponding to the detected coordinate from the parameter table, and sets the extracted gain in the first control unit.

7. The wearable action assisting device according to claim 1,
wherein the second storage unit stores input guide information indicating regions depending on a plurality of symptoms or a plurality of purpose actions, and
the display unit displays a region based on the input guide information together with the coordinate axes.

8. An interface device in a wearable action assisting device, the interface device for receiving an instruction of adjusting power to the wearable action assisting device, the wearable action assisting device comprising a drive source configured to give power to a wearer, a first detection unit configured to detect a biological potential signal along with a muscle activity of the wearer, a second detection unit configured to detect an angle of a joint of the wearer, a first control unit configured to perform a signal processing including a filter processing and amplification on the biological potential signal and to generate a first instruction signal for generating power depending on the biological potential signal after the signal processing on the drive source, a first storage unit configured to store reference parameters of joint angles of the wearer corresponding to a phase configuring a task classifying an action pattern of the wearer therein, a second control unit configured to compare a joint angle detected by the second detection unit with said reference parameters thereby to specify a phase of an action pattern of the wearer, and to generate a second instruction signal for generating power depending on the phase on the drive source, a combination unit configured to combine the first instruction signal and the second instruction signal to generate a combined instruction signal, a generation unit configured to generate a drive current based on the combined instruction signal and supply it to the drive source, a second storage unit configured to store a parameter table defining a correspondence between a coordinate and parameters of the signal processing in the first control unit, and a setting unit configured to extract parameters corresponding to a given coordinate from the parameter table, and set the extracted parameters in the first control unit,
the interface device comprising:
a display unit having a screen displaying thereon a coordinate axis corresponding to a strength of power given to the wearer by the drive source;
an input unit configured to input an arbitrary designated position in the screen;
a third detection unit configured to detect the coordinate of the designated position; and
a communication unit configured to transmit the detected coordinate to the setting unit.

9. A computer readable medium causing a computer to function as an interface device, the computer readable media comprising:
a program for receiving an instruction to adjust the power to a wearable action assisting device and causing an adjustment of the power to the wearable action assisting device in response to the instruction, the wearable action assisting device comprising a drive source configured to give power to a wearer, a first detection unit configured to detect a biological potential signal along with a muscle activity of the wearer, a second detection unit configured to detect an angle of a joint of the wearer, a first control unit configured to perform a signal processing including a filter processing and amplification on the biological potential signal and to generate a first instruction signal for generating power depending on the biological potential signal after the signal processing on the drive source, a first storage unit configured to store reference parameters of joint angles of the wearer corresponding to a phase configuring a task classifying an action pattern of the wearer therein, a second control unit configured to compare a joint angle detected by the second detection unit with said reference parameters thereby to specify a phase of an action pattern of the wearer, and to generate a second instruction signal for generating power depending on the phase on the drive source, a combination unit configured to combine the first instruction signal and the second instruction signal to generate a combined instruction signal, a generation unit configured to generate a drive current based on the combined instruction signal and supply it to the drive source, a second storage unit configured to store a parameter table defining a correspondence between a coordinate and parameters of the signal processing in the first control unit, and a setting unit configured to extract parameters corresponding to a given coordinate from the parameter table, and set the extracted parameters in the first control unit;
the program further causing a computer to
(i) display a coordinate axis corresponding to a strength of power given to the wearer by the drive source on a screen of a display unit,
(ii) accept input of an arbitrary designated position on the screen,
(iii) detect the coordinate of the designated position, and
(iv) transmit the detected coordinate to the setting unit.

* * * * *